US00PP33646P2

(12) United States Plant Patent
Kirwan

(10) Patent No.: US PP33,646 P2
(45) Date of Patent: Nov. 16, 2021

(54) ***AGLAONEMA* PLANT NAMED 'OSVAGI'**

(50) Latin Name: **Interspecific *Aglaonema* hybrid**
Varietal Denomination: OSVAGI

(71) Applicant: ForemostCo., Inc., Miami, FL (US)

(72) Inventor: David Kirwan, Winter Garden, FL (US)

(73) Assignee: ForemostCo., Inc., Miami, FL (US)

( * ) Notice: Subject to any disclaimer, the term of this patent is extended or adjusted under 35 U.S.C. 154(b) by 0 days.

(21) Appl. No.: 16/924,357

(22) Filed: Jul. 9, 2020

(51) Int. Cl.
*A01H 5/12* (2018.01)
*A01H 6/10* (2018.01)

(52) U.S. Cl.
USPC ..... Plt./376

(58) Field of Classification Search
USPC ..... Plt./376
See application file for complete search history.

*Primary Examiner* — Susan McCormick Ewoldt
(74) *Attorney, Agent, or Firm* — The Webb law Firm

(57) ABSTRACT

A new and distinct *Aglaonema* plant having green and red colored leaves and green colored stems.

3 Drawing Sheets

Botanical classification: Interspecific *Aglaonema* hybrid.
Varietal denomination: 'OSVAG1'.

BACKGROUND OF THE INVENTION

The present invention comprises a new and distinct variety of *Aglaonema* plant having the varietal name of 'OSVAG1'. 'OSVAG1' is the result of a cross conducted in Costa Rica between *Aglaonema* hybrid variety known as "Dizzy Diamond" (female parent, unpatented) and *Aglaonema* hybrid variety known as "Jasper Jones" (male parent, unpatented). The new variety was selected in August of 2018 in Costa Rica. Asexual reproductions of the new variety by cuttings first occurred in April of 2019. The new variety is similar to its female parent in overall plant shape, leaf shape, and having upright and outwardly turned leaves. However, "Dizzy Diamond" exhibits pink and green colored leaves. The new variety is similar to its male parent in having an acute leaf apex and base, but the overall leaf shape of "Jasper Jones" is lanceolate. 'OSVAG1' has been trial and field tested and has been found to retain its distinctive characteristics and remain true to type through successive propagations. The present invention has not been evaluated under all possible environmental conditions. The phenotype may vary with variations in environment without a change in the genotype of the plant.

Similar to an unnamed and unpatented *Aglaonema* variety known to the breeder, 'OSVAG1' exhibits green colored stems, petioles, and inflorescences. However, the varieties differ in that the leaves of the comparison variety have more red color present with defined green margins and the older leaves of 'OSVAG1' have a dark red color present. When compared to *Aglaonema* variety named 'OSVAG2' (U.S. Plant patent application Ser. No. 16/924,393), the new variety is similar in leaf size and shape. However, 'OSVAG2' exhibits pink and green colored leaves instead of red and green colored leaves. Further, the following characteristics distinguish 'OSVAG1' from other *Aglaonema* varieties known to the breeder:

Green colored stems, petioles, and inflorescences;
Mostly green colored leaf midribs with some red coloration present; and
Red colored speckles present between the venation.

DESCRIPTION OF THE DRAWINGS

The accompanying photographic drawings taken at approximately 18 months of age illustrate the new variety, with the colors being as nearly true as is possible with color illustrations of this type.

DESCRIPTION OF THE PLANT

Figure 1:
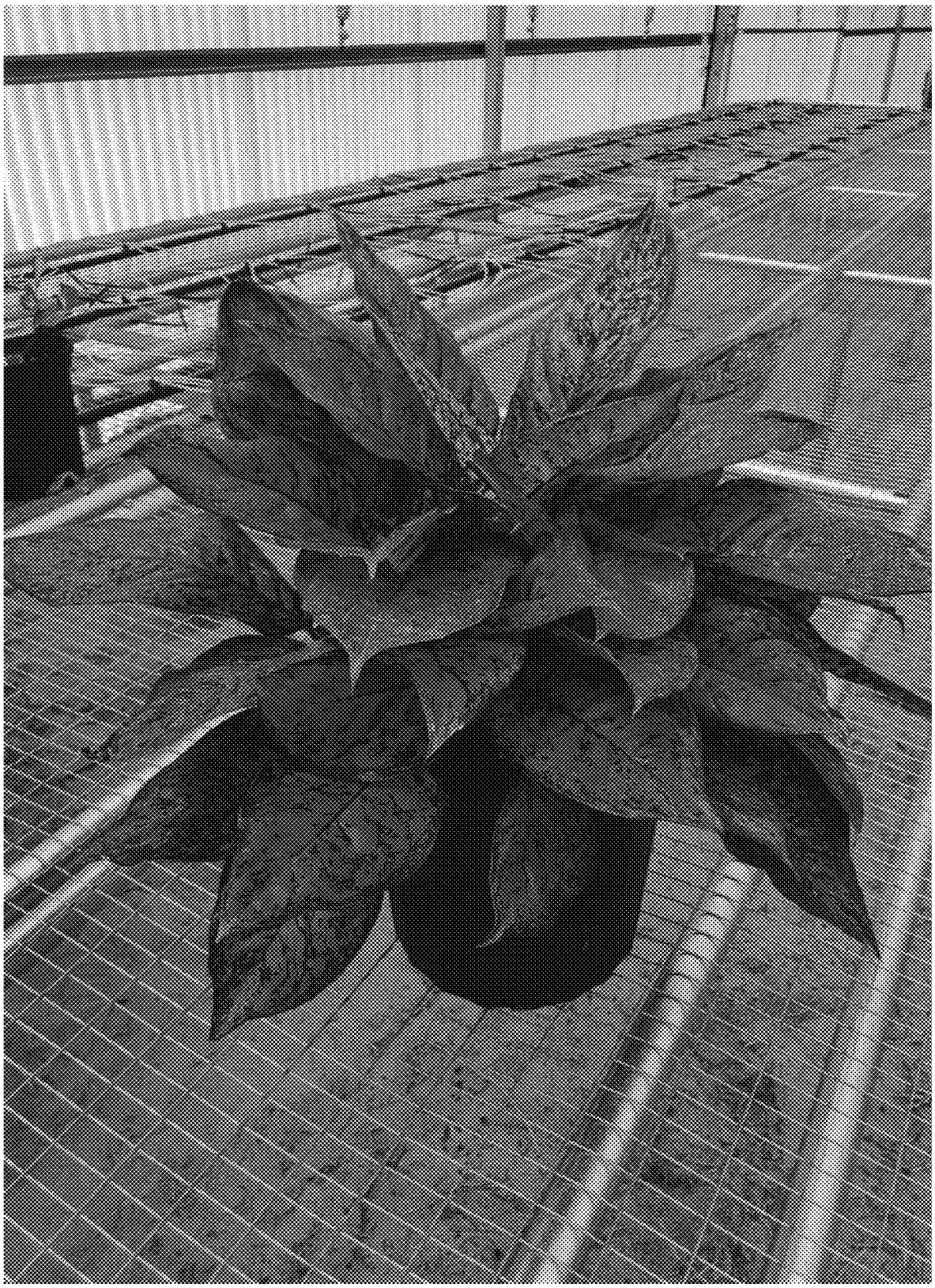
FIG. 1 shows a plant of the new variety.
Figure 2:
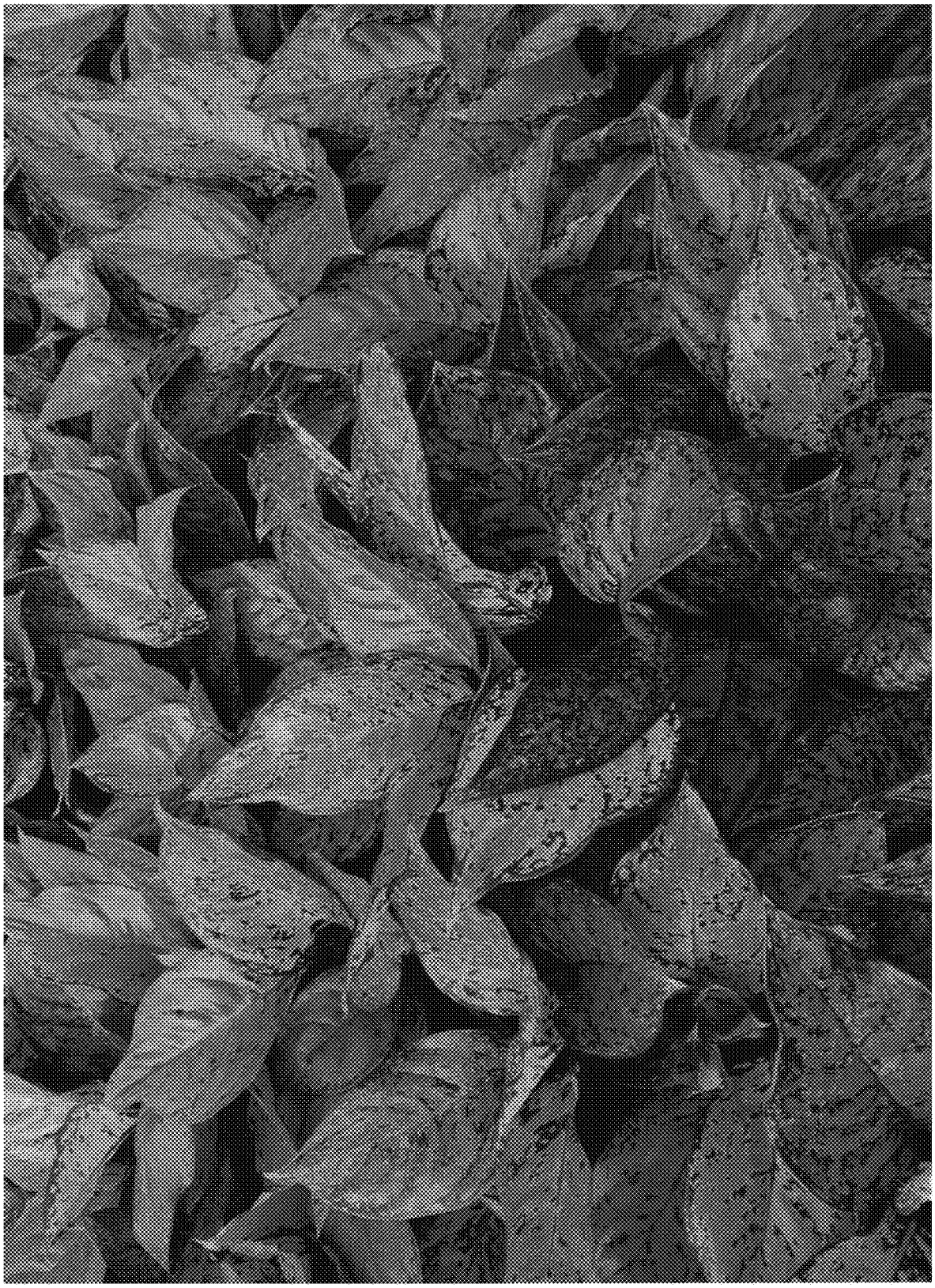
FIG. 2 shows a close-up view of the foliage of multiple plants of the new variety.
Figure 3:
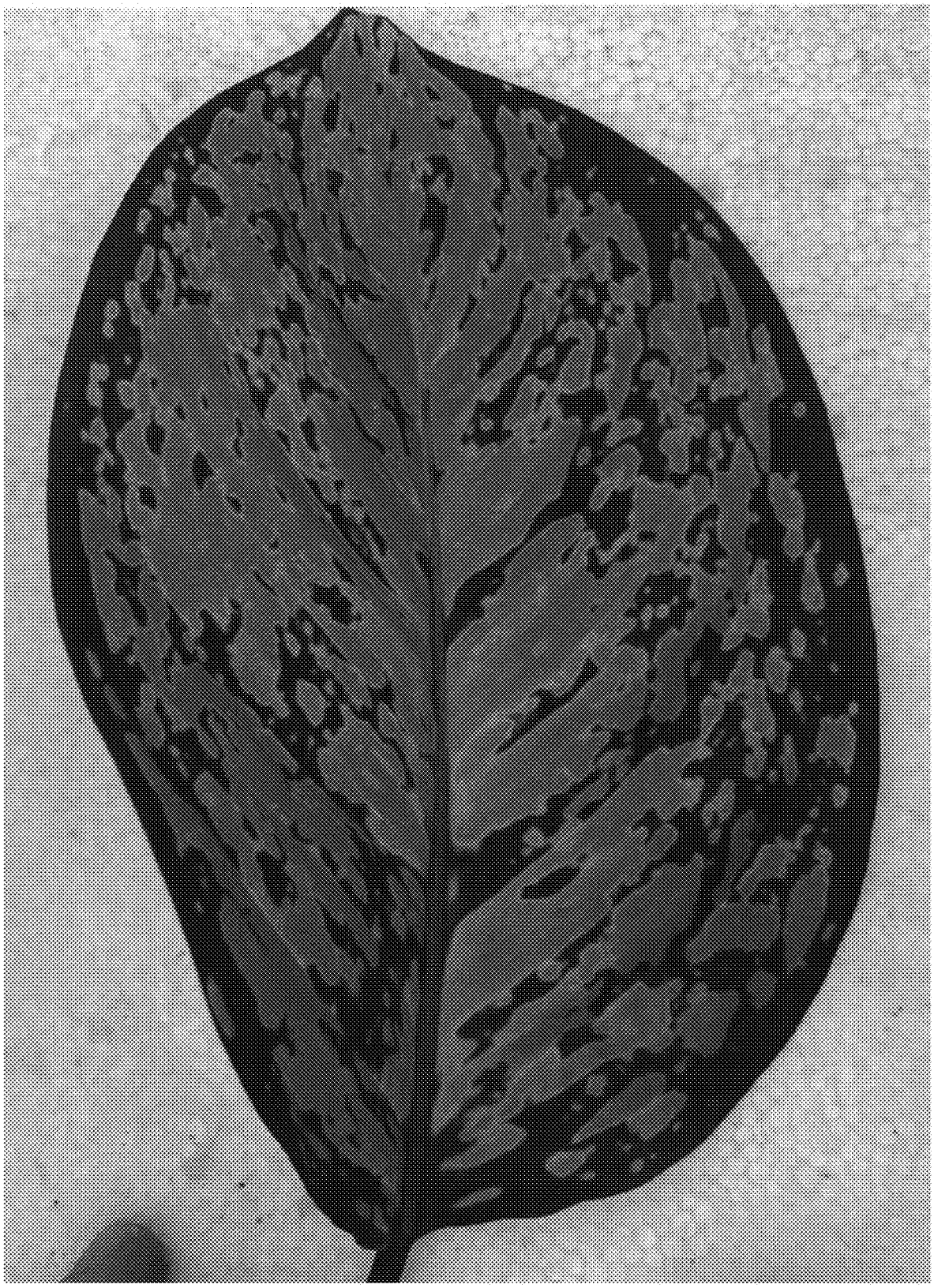
FIG. 3 shows a close-up view of the upper leaf surface of the new variety.

The following detailed description sets forth the characteristics of the new variety at approximately 18 months of age. The data which defines these characteristics was collected in a greenhouse in June of 2020 in Miami, Fla. Plants of the new variety were grown under 2,500 foot candles of artificial light in 2 gallon pots in a greenhouse in Miami, Fla. having 70% relative humidity and average temperatures from 18-29° C. Color references are primarily to the Munsell Plant Tissue Color Book, 2019 publication, except where general color terms are used.

PLANT

Time to initiate roots: About 25 days at about 26° C.
Time to develop roots: About 25 days at about 26° C.
Time to produce a finished plant from a rooted cutting: About 8 weeks in a 15 cm container.
Rooting habit and description: Roots spread out from the side and are 2.5Y 8/4, 7.5R 5/8 and 2.5 GY 6/6 in color.
Form: Spreading.
Height from media surface to top of foliage: 30.5 cm.
Height from media surface to top of inflorescence: 25.4 cm.

Plant diameter: 50.8 cm.
Plant shape: Clumping, with upright and outwardly turned leaves.
Vigor: Strong.
Strength: Pliable, with no need for artificial support.
Disease resistance/susceptibility: Susceptible to *Erwinia*.
Pest resistance/susceptibility: Susceptible to mealybugs.
Temperature tolerance: Sensitive to temperatures below 18° C. or above 29° C.
Drought tolerance: None.
Seeds/fruit: None present.
Stem:
*Average number/clumps of leaves per plant.*—7.
*Aspect.*—Vertical and upright and turned outward about 40°.
*Length.*—14.0 cm.
*Diameter.*—1.3 cm.
*Shape.*—Vertical column.
*Color.*—Green (5GY 5/6).
*Texture.*—Smooth and leathery.
*Strength.*—Sturdy, but pliable.
*Internode length.*—3.2 cm.
Leaves:
*Arrangement.*—Opposite.
*Average number per plant.*—10.
*Length.*—18.5 cm.
*Width.*—12.1 cm.
*Shape of leaf (generally).*—Ovate.
*Shape of apex.*—Acute.
*Shape of base.*—Acute.
*Margin description.*—Entire.
*Aspect.*—Symmetric.
*Texture and luster.*—Upper surface: Smooth and leathery with creases along the veins and a silky luster. Lower surface: Smooth and leathery with creases along the veins and a silky luster.
*Pubescence.*—Upper surface: None present. Lower surface: None present.
*Fragrance.*—None present.
*Color.*—Young leaves: Upper surface: Green and red (5R 3/10 — spotting along the veins; 7.5GY 3/4 — along the margins and surrounding spotting; and 7.5GY 4/6 — bordering the spotting). Lower surface: Green and red (2.5R 5/6 — spotting in between the veins, closer to the margin; 2.5R 6/6 — spotting in between the veins, closer to the midrib; 7.5GY 3/4 — along the margin; and 7.5GY 6/6 — along the midrib). Mature leaves: Upper surface: Green and red (5R 3/10 — spotting along the veins of entire leaf; 7.5GY 3/4 — along the margins and surrounding spotting; and 7.5GY 4/6 — bordering the spotting). Lower surface: Green and red (2.5R 6/6 — spotting along the veins, closer to the margin; 2.5R 7/4 — spotting along the veins, closer to the midrib; 7.5GY 3/4 — along the margin; and 7.5GY 4/6 — along the midrib).
*Veins.*—Venation pattern: Pinnate. Color: Upper surface: Green and red (5R 3/10, 7.5GY 3/4 and 7.5GY 4/6). Lower surface: Green and red (2.5R 5/6, 2.5R 6/6, 7.5GY 3/4 and 7.5GY 6/6).
Petioles:
*Aspect.*—Upright, with a 40-45° upward turn.
*Length.*—12.1 cm.
*Diameter.*—1.4 cm.
*Color.*—Green (5GY 5/6).
*Strength.*—Strong and lightly flexible.
*Wing.*—Not present.

INFLORESCENCE DESCRIPTION

Buds:
*Shape.*—Oval; egg-shaped.
*Length of an individual bud.*—4.6 cm.
*Diameter of an individual bud.*—1.3 cm.
*Color.*—Green (5GY 5/6).
*Texture.*—Smooth and leathery.
Inflorescences:
Natural flowering season: Year-round in Miami, Fla.
Blooming habit: Continuous.
Inflorescence arrangement: Spadix in spathe.
Orientation at opening: Circular opening from the side.
Inflorescence position: Tends to form below the foliage, but sometimes above.
Number of inflorescences per plant: 2-3.
Lastingness of an individual flower: 5 weeks or more.
Inflorescence length: 3.8 cm.
Inflorescence diameter: 1.3 cm.
Flowers:
*Type.*—Simple.
*Length.*—4.1 cm.
*Diameter.*—2.3 cm.
*Depth.*—1.7-1.9 cm.
Spathe:
*Length.*—3.8 cm.
*Width.*—5.1 cm.
*Color.*—5GY 5/6 (inner and outer surfaces).
Spadix:
*Length.*—3.0 cm.
*Diameter.*—1.0 cm.
*Color.*—5Y 8/12.
Peduncle:
*Length.*—3.8 cm.
*Diameter.*—1.3 cm.
*Color.*—5GY 5/6.
Petals: Not applicable.
Fragrance: None present.

REPRODUCTIVE ORGANS

Stamens:
*Number.*—About 13.
*Filament.*—Length: 0.5 cm. Color: 5Y 8/12.
*Anthers.*—Shape: Circular. Length: 0.1 cm. Color: 5Y 8/12.
*Pollen.*—Color: 5Y 8/12. Amount: Not visible to the naked eye.
Pistils:
*Number.*—More than 250.
*Length.*—0.6 cm.
*Style.*—Length: 0.6 cm. Color: 2.5Y 8/4.
*Stigma.*—Shape: Capitate. Color: 2.5Y 8/4. Size: Small.
*Ovaries.*—Position: Inferior — attached beneath flowers. Length: Under 0.01 cm. Width: Under 0.01 cm. Color: 2.5Y 8/4.

I claim:

1. A new and distinct variety of *Aglaonema* plant, as is herein illustrated and described.

* * * * *